(12) United States Patent
Govari et al.

(10) Patent No.: US 9,089,254 B2
(45) Date of Patent: Jul. 28, 2015

(54) SYNCHRONIZATION OF MEDICAL DEVICES VIA DIGITAL INTERFACE

(75) Inventors: Assaf Govari, Haifa (IL); Andres Claudio Altmann, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 484 days.

(21) Appl. No.: 12/200,431

(22) Filed: Aug. 28, 2008

(65) Prior Publication Data

US 2010/0056871 A1 Mar. 4, 2010

(51) Int. Cl.
| | |
|---|---|
| *H04J 3/06* | (2006.01) |
| *A61B 5/00* | (2006.01) |
| *A61B 5/06* | (2006.01) |
| *G06F 19/00* | (2011.01) |

(52) U.S. Cl.
CPC ............. *A61B 5/0002* (2013.01); *A61B 5/06* (2013.01); *G06F 19/3412* (2013.01)

(58) Field of Classification Search
CPC .. H04B 7/2125; H04B 7/2662; H04B 7/2126; H04W 56/00; H04W 56/0045; H04J 2011/0096; A61B 5/002; A61B 5/06; G06F 19/3412
USPC .............. 370/350, 395.62, 503, 507, 509–51, 370/324
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,558,091 A | 9/1996 | Acker et al. | |
| 6,128,290 A * | 10/2000 | Carvey | 370/347 |
| 6,172,499 B1 | 1/2001 | Ashe | |
| 6,177,792 B1 | 1/2001 | Govari et al. | |
| 6,233,476 B1 | 5/2001 | Strommer et al. | |
| 6,266,551 B1 | 7/2001 | Osadchy et al. | |
| 6,690,963 B2 | 2/2004 | Ben-Haim et al. | |
| 6,788,967 B2 | 9/2004 | Ben-Haim et al. | |
| 7,321,837 B2 | 1/2008 | Osorio et al. | |
| 7,846,150 B2 * | 12/2010 | Hamel et al. | 606/1 |
| 2002/0045809 A1 | 4/2002 | Ben-Haim | |
| 2006/0140139 A1 * | 6/2006 | DiSilvestro et al. | 370/310 |
| 2007/0016007 A1 | 1/2007 | Govari et al. | |
| 2007/0135692 A1 | 6/2007 | Hwang et al. | |

(Continued)

FOREIGN PATENT DOCUMENTS

| | | |
|---|---|---|
| EA | 007308 B1 | 8/2006 |
| JP | 2004-500217 | 1/2004 |

(Continued)

OTHER PUBLICATIONS

Partial European Search Report completed Dec. 28, 2009 for corresponding Application No. EP09252076.

(Continued)

*Primary Examiner* — Brenda H Pham
(74) *Attorney, Agent, or Firm* — Louis J. Capezzuto

(57) ABSTRACT

A method for device control includes bringing a plurality of medical devices into contact with a body of a patient. The medical devices are coupled to communicate with a console via a digital interface. A message is transmitted over the digital interface from the console, to be received simultaneously by the plurality of the medical devices. The medical devices are synchronized with one another responsively to receiving the message.

20 Claims, 2 Drawing Sheets

(56) References Cited

U.S. PATENT DOCUMENTS

| | | |
|---|---|---|
| 2007/0270642 A1 | 11/2007 | Bayer et al. |
| 2009/0131762 A1* | 5/2009 | Pelzek et al. ............ 600/301 |
| 2009/0248036 A1* | 10/2009 | Hoffman et al. ............ 606/130 |

FOREIGN PATENT DOCUMENTS

| | | |
|---|---|---|
| JP | 2004-283601 | 10/2004 |
| JP | 2007-021218 | 2/2007 |
| RU | 2096995 C1 | 11/1997 |
| RU | 2234238 C2 | 8/2004 |
| WO | WO 97/29678 | 8/1997 |
| WO | WO 01/78594 A1 | 10/2001 |
| WO | WO 03/105682 A1 | 12/2003 |
| WO | WO 2007/136859 A2 | 11/2007 |

OTHER PUBLICATIONS

Search Report issued by the People's Republic of China dated Sep. 25, 2012 for corresponding Patent Application No. 200910172829.9.
EP Search Report 09 25 2076 Dated Dec. 28, 2009.
EP 09 25 2076 Examination Report Dated Oct. 8, 2012.
JP 2009-196388 Office Action Dated Oct. 1, 2013.
RU 2009132436 Decision on Grant Refs Cited Feb. 11, 2014.

* cited by examiner

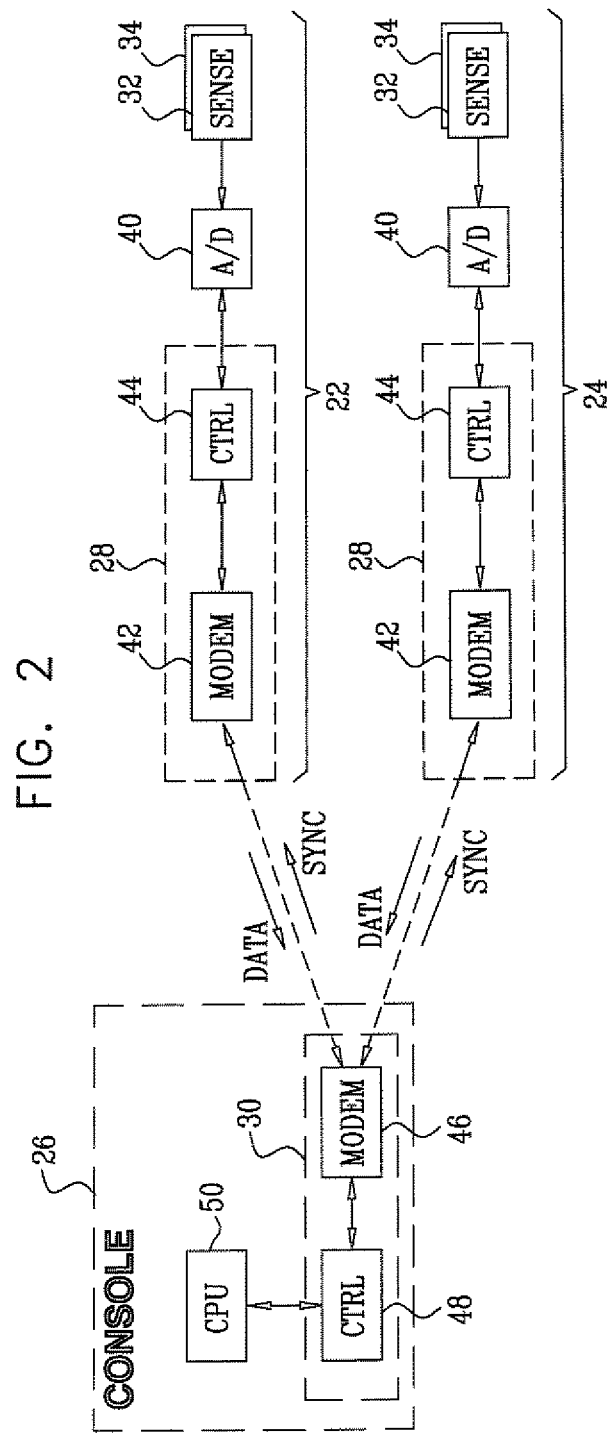

SYNCHRONIZATION OF MEDICAL DEVICES VIA DIGITAL INTERFACE

FIELD OF THE INVENTION

The present invention relates generally to electronic medical devices, and specifically to methods and systems for control of such devices.

BACKGROUND OF THE INVENTION

Many types of medical diagnostic and therapeutic systems comprise one or more probes, which contact the patient's body, and a control console, which receives signals and, in some cases, controls the functions of the probes. For example, cardiac catheters that are used for invasive diagnosis and treatment are typically configured in this way. In systems known in the art, such catheters are generally connected to the control console by a wired analog interface. Newer catheters, however, may communicate with the console via a wireless interface.

For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with signal processing and/or computer apparatus using wireless communication methods, such as IR (infra red), RF (radio frequency) or acoustic transmissions. One benefit of this type of configuration is that the catheter, which is inserted into the (electrically sensitive) heart can easily be made electrically floating. Another benefit is a reduction in the amount of cabling and wiring in which an operator might get entangled and/or accidentally pull out of the body. Still another advantage is the ease of sterilizing and maintaining the sterility of such a catheter, since the entire catheter may be sterilized as a single unit.

Another example of a wireless medical sensing device is a wireless ECG patch, developed by IMEC (Leuven, Belgium). The core of the wireless ECG patch consists of a miniaturized wireless sensor node integrated on a flexible substrate. It includes a commercial microprocessor enabling local digital signal processing, a 2.4 GHz radio link and a miniaturized rechargeable battery. In addition, the sensor node features a fork-antenna and a snap-on connector (for connection to an electrode). The wireless ECG patch can work in continuous monitoring mode, in which ECG- or EMG-data is continuously transmitted to a receiver, at a sample frequency between 250 and 1000 Hz. Further details of this device are described on the IMEC.be Web site.

SUMMARY OF THE INVENTION

Embodiments of the present invention provide improved methods and system for control of medical devices via a digital interface. In particular, some of these embodiments provide methods for synchronizing medical devices using messages transmitted over a standard digital interface, which may be wired or wireless.

There is therefore provided, in accordance with an embodiment of the present invention, a method for device control, including:

bringing a plurality of medical devices into contact with a body of a patient;

coupling the medical devices to communicate with a console via a digital interface;

transmitting a message over the digital interface from the console, to be received simultaneously by the plurality of the medical devices; and synchronizing the medical devices with one another responsively to receiving the message.

In a disclosed embodiment, the medical devices include catheters, which are brought into contact with a heart of the patient.

In some embodiments, the digital interface includes a wireless interface. In one embodiment, transmitting the message includes sending a broadcast message, in a format prescribed a standard applicable to the wireless interface, from the console to the plurality of the medical devices Alternatively or additionally, transmitting the message includes sending a synchronization message in accordance with a first protocol, and the method includes transmitting data over the wireless interface using a second protocol, different from the first protocol.

In one embodiment, transmitting the message includes sending one or more pulses from the console to the plurality of the medical devices.

In some embodiments, the medical devices include respective sensors, which are configured to generate signals while the medical devices are in contact with the body, and the method includes sampling the signals in the medical devices, and transmitting the sampled signals to the console over the digital interface. Typically, the signals are sampled using a respective internal clock in each of the medical devices, and synchronizing the medical devices includes resetting the internal clock.

In a disclosed embodiment, the respective sensors include position sensors, and the signals are indicative of respective positions of the medical devices. Additionally or alternatively, the respective sensors include electrodes, and the signals are indicative of electrical activity in the body and/or a contact impedance between the devices and tissue in the body. Further additionally or alternatively, the respective sensors are responsive to force exerted on the devices, and the signals are indicative of a contact pressure between the device and tissue in the body.

There is also provided, in accordance with an embodiment of the present invention, medical electronic apparatus, including:

a console, which includes a first digital interface and is configured to transmit a message over the digital interface simultaneously to multiple recipients; and a plurality of medical devices, which are configured to be brought into contact with a body of a patient, and which include second digital interfaces for communication with the first digital interface of the console, and which are configured to simultaneously receive the message transmitted by the console and to synchronize with one another responsively to receiving the message.

The present invention will be more fully understood from the following detailed description of the embodiments thereof, taken together with the drawings in which:

BRIEF DESCRIPTION OF THE DRAWINGS

FIG. 2 is a block diagram, which schematically illustrates functional components of a medical system that comprises a wireless digital interface, in accordance with an embodiment of the present invention.

DETAILED DESCRIPTION OF EMBODIMENTS

Figure 1:
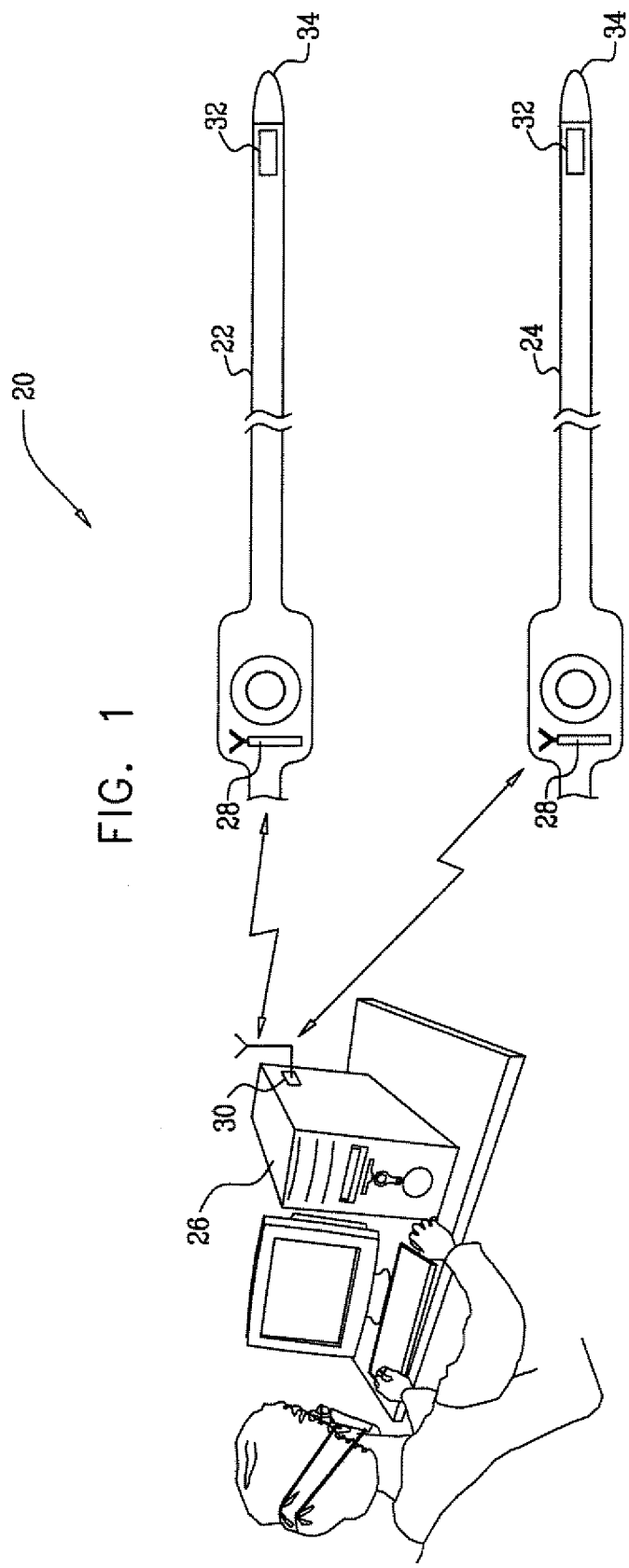
FIG. 1 is a schematic, pictorial illustration of a medical system that comprises a wireless digital interface, in accordance with an embodiment of the present invention.

In embodiments of the present invention that are described in this patent application, medical devices, such as cardiac catheters, communicate with a console via a standard digital interface, which may be wired or wireless. Internal operating circuits within each such medical device control the functional elements of the device and digitize signals captured by the device for transmission to the console. The use of a standard digital interface in this context is advantageous in reducing cost and enhancing system flexibility, but such standard interfaces often provide only a single channel for messages (data and control) between the console and the medical device.

In some procedures, multiple devices may be used and interface simultaneously with the same console. For accurate registration between the signals transmitted by the devices to the console, it is desirable that the internal clocks of the different devices be mutually synchronized. In embodiments of the present invention, this synchronization is provided by transmitting a synchronization message simultaneously from the console to all of the devices. For example, when the devices communicate with the console over Bluetooth™ wireless links, the console may transmit a standard Bluetooth broadcast message in order to synchronize the catheters. The synchronization message may be transmitted over the same channel that is used for data communications. The device operating circuits are programmed to recognize and synchronize to the broadcast message.

FIG. 1 is a schematic, pictorial illustration of a medical system 20 that uses a wireless digital interface in accordance with an embodiment of the present invention. For the sake of clarity, this figure, as well as FIG. 2, shows only a limited number of physical and functional components of system 20 that are useful in understanding the operation of this embodiment of the present invention. The remaining elements that are needed to build a working system depend on the specific target application and configuration of the system and will be apparent on this basis to those skilled in the art.

System 20 in this example is a cardiac catheterization system, which includes at least two catheters 22, 24 for insertion into the heart of a patient. The catheters each comprise a wireless digital interface 28, which communicates with a corresponding interface 30 in a console 26. Interfaces 28 and 30 may operate in accordance with any suitable wireless communication standard that is known in the art, such as Bluetooth, one of the IEEE 802.11 family of standards, or the HiperLAN standard.

Console 26 in the example shown in FIG. 1 comprises a general-purpose computer, which is equipped with interface 30 and suitable circuits and software for controlling and collecting data from catheters 22 and 24. More generally, however, the term "console" is used in the context of the present patent application and in the claims to denote any sort of control unit with a suitable processor and interface for controlling and receiving signals from a medical device that is in contact with a patient's body. This sort of console may be of substantially any suitable scale, from a major instrumentation system to a small handheld or tabletop device.

Catheters 22 and 24 each comprise one or more sensors, which in this example include a position sensor 32 and an electrode 34. The electrode is used to sense electrical signals inside the heart. Alternatively or additionally, the electrode may be used for therapeutic purposes, such as delivering radio frequency (RF) energy to the endocardium for ablation-based treatment of arrhythmias. As another alternative, electrode 34 may be used to sense contact impedance between the catheter and the heart tissue.

Position sensor 32 generates signals that are indicative of the position coordinates (location and/or orientation) of the respective catheter within the patient's body. The position sensor may implement any suitable method of position sensing that is known in the art. For example, the position sensor may sense magnetic fields generated by field generator coils (not shown) at known locations outside the patient's body, as in the CARTO™ system, produced by Biosense Webster Inc. (Diamond Bar, Calif.). Suitable methods for magnetic field-based position sensing are further disclosed in U.S. Pat. Nos. 5,391,139, 5,443,489, and 6,788,967 to Ben-Haim, in U.S. Pat. No. 6,690,963 to Ben-Haim, et al., in U.S. Pat. No. 5,558,091 to Acker et al., in U.S. Pat. No. 6,172,499 to Ashe, and in U.S. Pat. No. 6,177,792 to Govari, whose disclosures are incorporated herein by reference.

Further alternatively or additionally, the catheters in system 20 may comprise other types of sensors of position and/or physical or physiological parameters, as are known in the art. For example, sensor 32 may comprise a force sensor or tactile sensor, which generates signals indicative of the contact pressure between the catheter and the heart tissue.

FIG. 2 is a block diagram, which schematically illustrates functional components of system 20, in accordance with an embodiment of the present invention. Sensors 32, 34 in each of catheters 22 and 24 are connected to interface 28 via an analog/digital (A/D) converter circuit 40. This circuit samples and digitizes the signals that are output by the sensors, using an internal sampling clock. Interface 28 comprises a modem 42 and a controller 44. The modem transmits data signals over the air to interface 30 in console 26 and receives control signals from interface 30, in accordance with the applicable communication standard. The controller formats data from circuit 40 in packets for transmission by the modem and carries out the commands conveyed by the control signals from console 26. The internal sampling clock used by circuit 40 may be generated either by controller 44 or by circuit 40 itself. Additionally or alternatively, controller 44 may use the internal clock to time-stamp the data packets that it transmits to the console.

Interface 30 in console 26 similarly comprises a modem 46 and a controller 48, which communicates with a central processing unit (CPU) 50. The CPU receives and processes the data signals conveyed from catheters 22 and 24 (including catheter position and cardiac electrical signals in the present example) in order to assemble a diagnostic output. For example, the CPU may produce a map of cardiac electrical activity, such as the type of map that is produced by the above-mentioned CARTO system.

CPU 50 may decide from time to time to synchronize the components of system 20. Typically, synchronization is performed at start-up of the system, and possibly repeated periodically thereafter. Such synchronization is desirable, for example, to ensure that the internal clocks that are used by circuit 40 in catheters 22 and 24 are synchronized with one another, so that the CPU can accurately correlate the signals in creating the diagnostic output. To synchronize catheters 22 and 24, CPU 50 issues a command to controller 48 to transmit a synchronization message over the air simultaneously from modem 46 to modems 42 in the catheters. Upon receiving the message, controllers 44 reset the internal clocks of the respective catheters, whereby the clocks are synchronized with one another to within a small tolerance.

The synchronization message may use a broadcast format that is mandated by the applicable wireless communication standard. For example, assuming interfaces 28 and 30 are configured as a Bluetooth piconet, with console 26 as the master and catheters 22 and 24 as slaves, the synchronization message may be transmitted using the active slave broadcast (ASE) mechanism that is defined in the Bluetooth specification. Alternatively, other one-to-many transmission mechanisms, provided by Bluetooth, as well as other standards, may be used for this purpose.

Alternatively, other types of synchronization messages may be used, whether over Bluetooth or over other types of standard or proprietary interfaces and protocols. For example, one protocol may be used to send the synchronization messages, while another protocol is used for transmitting data between the catheters and the console. If a suitable proprietary protocol is used, the synchronization message may be as simple as a predefined sequence of pulses, or even a single pulse, transmitted over the interface.

In some embodiments, there may even be separate transceivers for data transfer and synchronization functions. Upon identifying a synchronization pulse, for example, this transceiver may send an interrupt to controller 44, which accordingly adjusts the time stamps of the packets that it transmits to the console.

The precision of the synchronization that is required depends on the sensing application. For ECG sensing, for example, the precision may be as coarse as 0.5 ms. For accurate position sensing, on the other hand, precision of 1 µs or better in synchronization is desirable. This sort of accuracy may not be available from existing wireless communication protocols, such as Bluetooth. For enhanced accuracy, the receiver circuit of modem 42 may be modified to permit detection of raw RF pulses before they are processed by the core circuits of the modem. The modified receiver circuit signals controller 44 when an RF pulse is detected, and the controller synchronizes the catheter circuits accordingly.

Although the embodiment described above relates specifically to cardiac catheters, the principles of the present invention are similarly applicable to other types of invasive and body-surface devices. Furthermore, the methods and circuits described above may be adapted to operate not only over various different types of wireless interfaces, but also over wired digital interfaces, such as a Universal Serial Bus (USB) interface.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art

The invention claimed is:

1. A method for device control, comprising:
bringing a plurality of medical devices into contact with a body of a patient, the medical devices comprising respective senors, which are configured to generate signals while the medical devices are in contact with the body;
coupling the medical devices to communicate with a console via a digital interface;
sampling the signals in the medical devices using a respective internal clock in each of the medical devices, and transmitting the sampled signals to the console over the digital interface, and;
transmitting a message over the digital interface from the console, to be received simultaneously by the plurality of the medical devices; and
synchronizing the medical devices with one another responsively to receiving the message by resetting the internal clock.

2. The method according to claim 1, wherein the medical devices comprise catheters, which are brought into contact with a heart of the patient.

3. The method according to claim 1 wherein the digital interface comprises a wireless interface.

4. The method according to claim 3, wherein transmitting the message comprises sending a broadcast message, in a format prescribed a standard applicable to the wireless interface, from the console to the plurality of the medical devices.

5. The method according to claim 3, wherein transmitting the message comprises sending a synchronization message in accordance with a first protocol, and wherein the method comprises transmitting data over the wireless interface using a second protocol, different from the first protocol.

6. The method according to claim 1, wherein transmitting the message comprises sending one or more pulses from the console to the plurality of the medical devices.

7. The method according to claim 1, wherein the respective sensors comprise position sensors, and the signals are indicative of respective positions of the medical devices.

8. The method according to claim 1, wherein the respective sensors comprise electrodes, and the signals are indicative of electrical activity in the body.

9. The method according to claim 1, wherein the respective sensors comprise electrodes, and the signals are indicative of a contact impedance between the devices and tissue in the body.

10. The method according to claim 1, wherein the respective sensors are responsive to force exerted on the devices, and the signals are indicative of a contact pressure between the device and tissue in the body.

11. Medical electronic apparatus, comprising:
a console, which comprises a first digital interface and is configured to transmit a message over the digital interface simultaneously to multiple recipients; and
a plurality of medical devices, which are configured to be brought into contact with a body of a patient, and which comprise second digital interfaces for communication with the first digital interface of the console, and which are configured to simultaneously receive the message transmitted by the console and to synchronize with one another responsively to receiving the message, the medical devices comprising respective sensors, which are configured to generate signals while the medical devices are in contact with the body, and circuitry, which is configured to sample the signals generated by the sensors, and to transmit the sampled signals to the console over the digital interface, wherein the circuitry is configured to sample the signals using a respective internal clock in each of the medical devices, and to reset the internal clock upon receiving the message.

12. The apparatus according to claim 11, wherein the medical devices comprise catheters, which are configured to be brought into contact with a heart of the patient.

13. The apparatus according to claim 11, wherein the first and second digital interfaces comprises wireless interfaces.

14. The apparatus according to claim 13, wherein the message comprises a broadcast message, which is transmitted from the console to the plurality of the medical devices in a format prescribed a standard applicable to the wireless interfaces.

15. The apparatus according to claim 13, wherein the message comprises sending a synchronization message in accordance with a first protocol, and wherein the medical devices are configured to transmit data over the wireless interface using a second protocol, different from the first protocol.

16. The apparatus according to claim 11, wherein the message comprises one or more pulses, which are transmitted from the console to the plurality of the medical devices.

17. The apparatus according to claim 3, wherein the respective sensors comprise position sensors, and the signals are indicative of respective positions of the medical devices.

18. The apparatus according to claim 3, wherein the respective sensors comprise electrodes, and the signals are indicative of electrical activity in the body.

19. The apparatus according to claim 3, wherein the respective sensors comprise electrodes, and the signals are indicative of a contact impedance between the devices and tissue in the body.

20. The method according to claim 3, wherein the respective sensors are responsive to force exerted on the devices, and the signals are indicative of a contact pressure between the device and tissue in the body.

* * * * *